(12) United States Patent
Eikefjord et al.

(10) Patent No.: US 11,004,359 B2
(45) Date of Patent: May 11, 2021

(54) DEFIBRILLATION TRAINING SYSTEM

(71) Applicant: Laerdal Medical AS, Stavanger (NO)

(72) Inventors: Arild Eikefjord, Sandnes (NO); Håkon Hodne, Kleppe (NO)

(73) Assignee: Laerdal Medical AS, Stavanger (NO)

( * ) Notice: Subject to any disclaimer, the term of this patent is extended or adjusted under 35 U.S.C. 154(b) by 95 days.

(21) Appl. No.: 15/565,985

(22) PCT Filed: Apr. 25, 2016

(86) PCT No.: PCT/EP2016/059131
§ 371 (c)(1),
(2) Date: Oct. 12, 2017

(87) PCT Pub. No.: WO2016/177591
PCT Pub. Date: Nov. 10, 2016

(65) Prior Publication Data
US 2018/0114465 A1     Apr. 26, 2018

(30) Foreign Application Priority Data
May 5, 2015   (GB) ..................... 1508031

(51) Int. Cl.
*G09B 23/28*       (2006.01)
*A61N 1/04*        (2006.01)
(52) U.S. Cl.
CPC .......... *G09B 23/288* (2013.01); *A61N 1/046* (2013.01); *A61N 1/0476* (2013.01); *A61N 1/0492* (2013.01)

(58) Field of Classification Search
CPC .... A61N 1/046; A61N 1/0492; A61N 1/0476; G09B 23/288
See application file for complete search history.

(56) References Cited

U.S. PATENT DOCUMENTS

| 5,611,815 A | * | 3/1997 | Cole ................... A61N 1/39 607/5 |
| 5,993,219 A | * | 11/1999 | Bishay .............. A61N 1/046 434/265 |
| 6,190,177 B1 | | 2/2001 | Thu et al. |
| 6,266,562 B1 | * | 7/2001 | Leyde ............ A61N 1/3937 607/5 |
| 6,319,011 B1 | * | 11/2001 | Motti ............... G09B 23/288 434/262 |
| 6,336,047 B1 | | 1/2002 | Thu et al. |

(Continued)

FOREIGN PATENT DOCUMENTS

| IN | 2602/CHE/2011 | 8/2011 |
| KR | 20130015751 A | 2/2013 |

(Continued)

OTHER PUBLICATIONS

Beauce, Gaetan, International Search Report, prepared for PCT/EP2016/059131, dated Jun. 15, 2016, three pages.

*Primary Examiner* — Steve Rowland
(74) *Attorney, Agent, or Firm* — Shackelford, Bowen, McKinley & Norton, LLP

(57) ABSTRACT

A defibrillation training system, enabling the use of a live defibrillation unit (2), comprising a module (3) and a cable (1) interconnecting said module (3) and said defibrillation unit (2). The cable (1) being a resistance cable that has an impedance that simulates patent impedance and absorbs electric shock pulses made by said defibrillator unit (2).

13 Claims, 6 Drawing Sheets

(56) References Cited

U.S. PATENT DOCUMENTS

Figure 1:
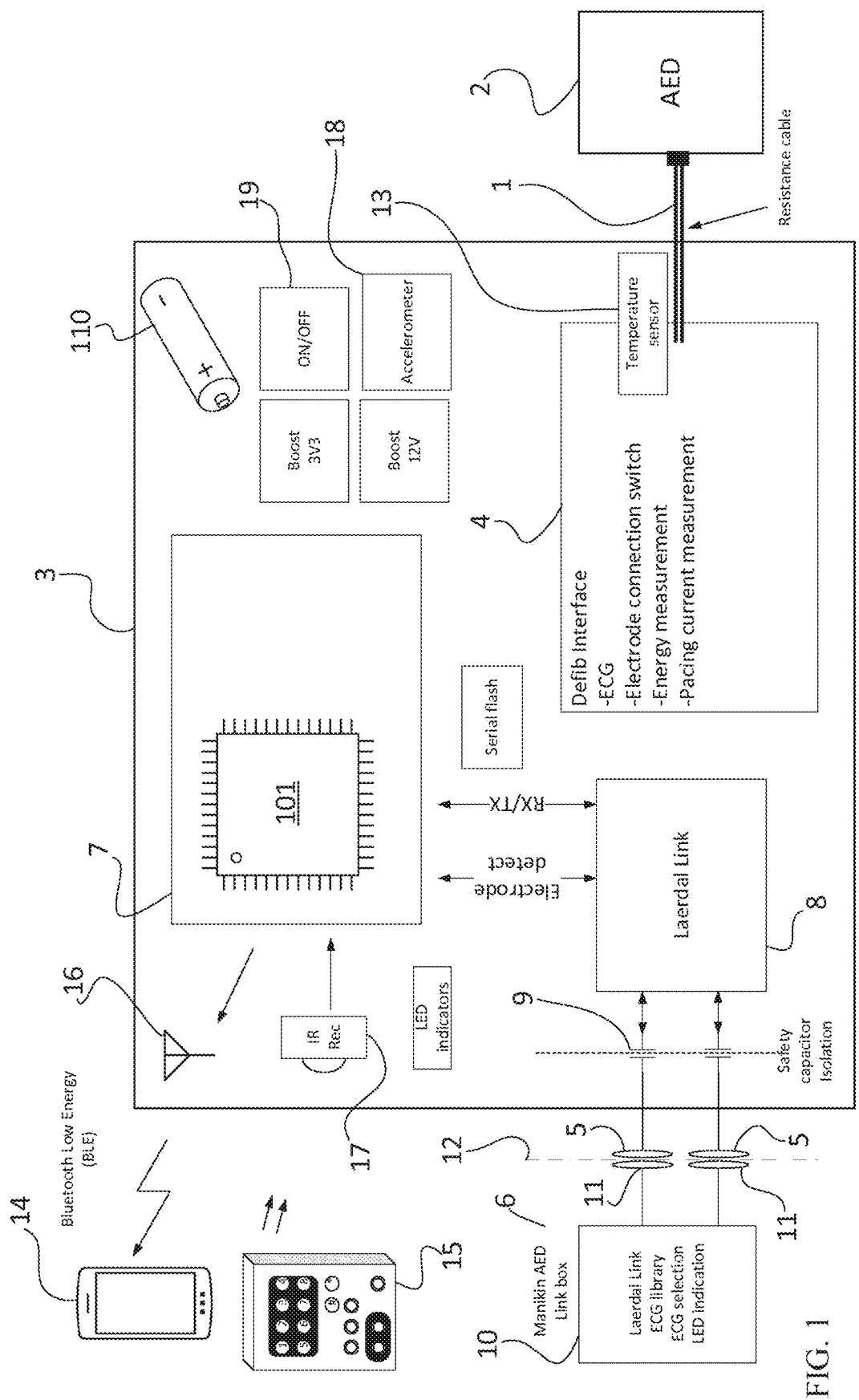

| | | | | |
|---|---|---|---|---|
| 6,356,785 B1 * | 3/2002 | Snyder | ...................... | A61N 1/39 |
| | | | | 607/5 |
| 6,377,845 B1 * | 4/2002 | Kinast | .................. | A61B 5/0428 |
| | | | | 600/547 |
| 6,872,080 B2 * | 3/2005 | Pastrick | ............... | G09B 23/288 |
| | | | | 434/262 |
| 7,715,913 B1 * | 5/2010 | Froman | .................... | A61N 1/39 |
| | | | | 607/5 |
| 2009/0029332 A1 * | 1/2009 | Solosko | .................. | A61N 1/39 |
| | | | | 434/265 |
| 2011/0106190 A1 * | 5/2011 | Foeller | ..................... | A61N 1/39 |
| | | | | 607/5 |
| 2013/0330698 A1 * | 12/2013 | Yang | .................... | G09B 23/288 |
| | | | | 434/265 |
| 2014/0004494 A1 * | 1/2014 | Griesser | ............... | A61N 1/3993 |
| | | | | 434/267 |
| 2014/0315173 A1 * | 10/2014 | Duval-Arnould | .... | G09B 23/288 |
| | | | | 434/262 |
| 2015/0325150 A1 * | 11/2015 | Petruzziello | ......... | G09B 23/288 |
| | | | | 434/267 |
| 2017/0076634 A1 * | 3/2017 | Hoss | .................... | G09B 23/288 |

FOREIGN PATENT DOCUMENTS

| WO | WO-2005078682 A1 * | 8/2005 | ............... | A61N 1/39 |
|---|---|---|---|---|
| WO | WO-2012127340 A1 * | 9/2012 | ........... | A61N 1/3993 |

* cited by examiner

DEFIBRILLATION TRAINING SYSTEM

The present invention relates to a system for training on using defibrillators. Training on the use of defibrillator is of utmost importance to health personnel, since time and accuracy are vital factors to a successful resuscitation. It is important that the defibrillation is done as quickly as possible when it is determined that defibrillation is needed, and it is important that the defibrillation pads are placed accurately on the chest of the patient.

The aim of the present invention is to provide for more realistic training on manikins.

Several types of training defibrillators are on the market, which are purely for training and cannot be used to give a patient an actual defibrillation shock. Some examples are shown in KR20130015751 and in IN20110260214 (2602/CHE/2011). These training defibrillators are very safe to use, as they are not capable of giving a shock, and merely simulates the shock. However, the training defibrillators should be as similar to a real (or live) defibrillator in all other aspects. This means that ideally there should be a training defibrillator for each model of the real thing. However, this would make it overly expensive for, e.g., a hospital to purchase training defibrillators.

Moreover, there is a risk, especially in a hospital, that a paramedic could try to use a training defibrillator in an actual resuscitation incident. A training defibrillator would of course be of no use in such a care, and valuable time would be lost.

There is also a risk that a live defibrillator would be used for training without the persons involved noticing that it is not a training defibrillator. As a real defibrillator is capable of giving out a high-energy shock, this poses danger for injury to persons if it is used erroneously, and for damage to equipment, such as a manikin, used in connection with the training.

There is also known training equipment that can be used for training with a live defibrillator.

Some defibrillators are prepared with a training mode. However, this does not apply to all defibrillator models. Moreover, there is a risk of persons being injured if the defibrillator is erroneously set to shocking mode in a training case, and that a patient will not get a shock if the defibrillator is set to training mode in a live resuscitation incident.

An example is shown in US2014/0315173, which describes a non-conductive belt that can be placed around the chest of a manikin. The belt is supposed to conduct defibrillation shocks so that the manikin is not damaged.

However, the shock will still be fed to the pads, or other contacts, that have been coupled to the belt. This means that there is still a risk that untrained persons can be injured if they are not handling the equipment properly. The belt that has to be wrapped around the manikin will also reduce the realistic impression of the training.

It is known from WO2012/127340 an adapter that can be connected between a defibrillator and a set of electrode pads. A shunt resistor either is placed inside of the adapter or can be connected to the adapter via a separate connection. A relay conducts the electric shock to the resistor. An optional safety resistor can also be arranged within the adapter in case shock voltage would leak towards the pads.

Although the drawings of WO2012/127340 shows the adapter as a fairly small item, it is a fact that the resistor must have a minimum size that would, if placed inside the adapter, make the adapter both bulky and heavy. If placed outside the adapter, this would make up another item that the trainer would have to remember to connect.

The fact that an adapter with a built in resistor is bulky, is evident from similar adapters marketed by Symbio Corporation under inter alia model names CS1201 and CS301 (http://www.symbiocorp.com/).

The resistor will inevitably heat up when exposed to a multiple of consecutive shocks. During training, the purpose is to allow the users to perform multiple training events. Therefore, there is a need for the resistor to be capable of conducting the heat away. Consequently, the adapter will have to be of a certain minimum size in order for the heat to dissipate without damaging the electronics within the adapter.

Other examples of prior art are U.S. Pat. Nos. 6,336,047 and 6,190,177, both belonging to the present proprietor. These references concern a system for communication between sensors in training equipment and electrodes of a defibrillator. This system enables the defibrillator to set itself automatically to training mode when it is connected to a manikin configured to send a signal to the defibrillator that identifies the manikin.

US 20090029332 A1 proposes a training adapter for defibrillators, however requires a training mode in the defibrillator.

Several of the existing solutions include a manikin that is adapted to work with live defibrillators, and which has visible connection studs on the chest skin and a load box inside the manikin that is capable of dissipating the energy from the defibrillation shock. This is unrealistic both in visible appearance and infringes the correct procedure for defibrillation treatment. If the connections to the studs on the manikin are not properly made, there is danger of damage to the equipment and also a fire hazard. If someone touches the studs during shocking, there is danger for an electric shock.

Therefore, there is a need for a new training adapter that can be used together with an actual defibrillator, which is small in size, light in weight, and is capable of simulating a patient, so that the defibrillator will "see" the adapter as a patient and operate accordingly.

This is achieved according to the invention by a defibrillation training system, enabling the use of a live defibrillation unit and a module connected to the defibrillation unit, a cable connecting said module and said defibrillation unit, wherein said cable is a resistance cable that has an impedance that simulates patient impedance and absorbs electric shock pulses made by said defibrillator unit.

Since the cable has a large surface area that is relatively large compared to the resistance value, the heat that is created from the defibrillation shock will quickly dissipate from the cable. The cable will heat up only marginally, even after several rapidly subsequent shocks.

The cable should have a total resistance that is compatible with normal human shock resistance values. An example of cable resistance suitable for dissipating a typical shock is a total resistance of about 120 Ohms over a length of about 100 cm in total. Since the cable is a two lead cable, each lead will have a resistance of about 60 Ohms and a length of about 50 cm.

In a preferred embodiment, the system comprises a set of training pads adapted to be coupled between said module and a training manikin, said training manikin having an electronic circuit capable of communicating with said training pads, said module having a galvanic isolation that isolated said training pads from said resistance cable, said module further having an electronic circuit capable of sensing when said training pads are in communication with said electronic circuit within said training manikin. Thereby, very realistic training on a manikin can be performed without risk.

In a further preferred embodiment, the module also has a measurement circuit that measures the defibrillation shock, said module also having a feedback circuit that provides ECG feedback to the defibrillation unit, both prior to and in response to the measured shock. This will further enhance the realistic training.

In an even further preferred embodiment, the system comprises a communication unit that, when a shock has been delivered to the module, communicates the fact that a shock has been delivered to the training manikin, and thus enable the manikin to respond clinically adequately to the shock condition, and that the manikin optionally has a storage to store a complete record of a training session. This enhances the training even further.

In a further embodiment, said module comprises an ECG generating circuit coupled to said defibrillating unit, said ECG generating circuit being coupled to said feedback circuit, and that said ECG generating unit generate ECG originating from the adapter, the manikin or a wireless unit. This will bring the realistic training to an even higher level.

If said module comprises a wireless communication circuit for communicating with a remote control device, the trainer can control the training situation without having to interfere physically with the training equipment.

If said remote control device receives information about the defibrillation shock and is capable providing patient reaction ECG data to said feedback circuit based on a selected medical scenario of a plurality of medical scenarios stored in said remote control device, the trainer is given an even better control of the training situation. It will also provide the possibility to quickly choose a scenario among the pre-sets.

Preferably, said module by a quick connector that allows disconnection of said defibrillating unit from said module. Thereby, the defibrillator can be connected and disconnected with ease. The latter is especially important if the defibrillator also must be available for live resuscitation when needed.

If the training pads are configured to form a capacitive or inductive coupling with electrodes inside the manikin, the manikin need not have any studs or visible contacts on its chest. This will further enhance the realistic training.

By arranging the electrodes inside the manikin under the skin of the manikin, is further ensured that there are no visible contacts on the surface of the manikin chest.

In a further embodiment, the system comprises a non-conductive cable to be connected between the adapter and the manikin. Thereby safe training options for passive/non-electronic manikins and training on human subjects can be provided.

Preferably, the adapter has a power-up circuit that detects the presence of a defibrillator impedance measurement signal and when said signal is present powers up said adapter. This removes the need for an external switch that may be triggered by a mistake or that the module inadvertently is left on to drain the batteries.

In an alternative embodiment, the adapter comprises an accelerometer capable of detecting its orientation and movement, and that a change in orientation or detection of movement beyond a pre-set level is used to trigger power-up of the adapter.

Figure 2:
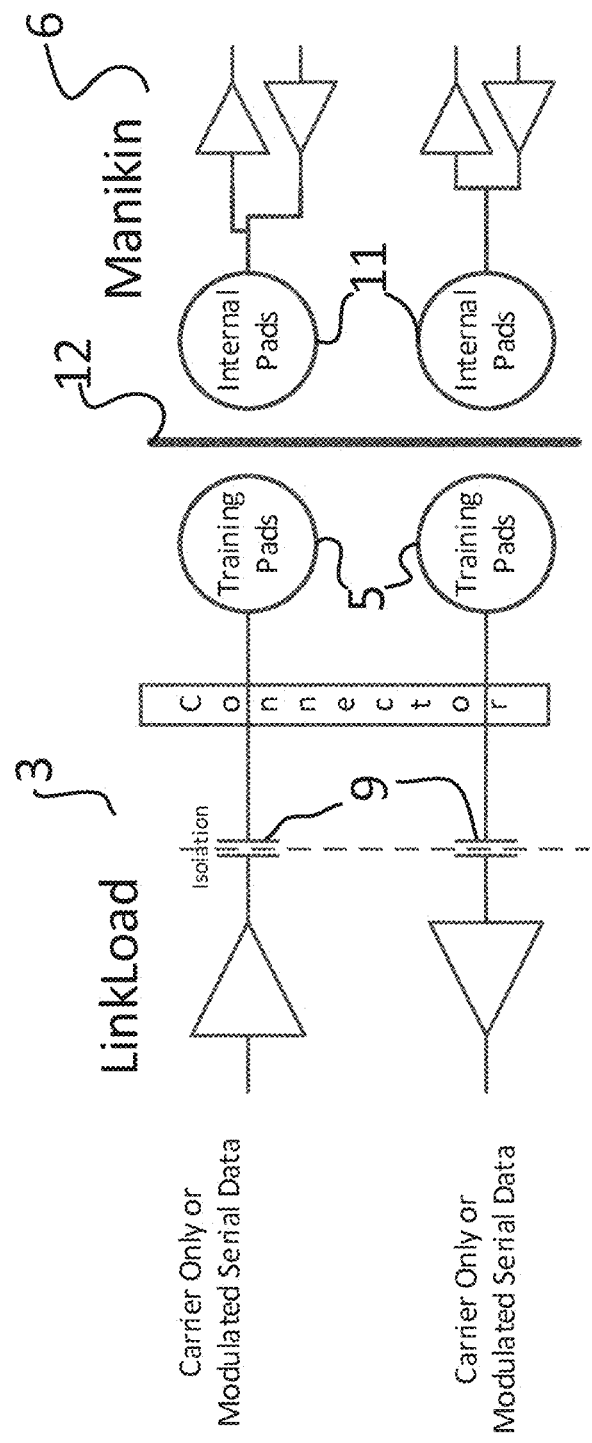
Figure 3:
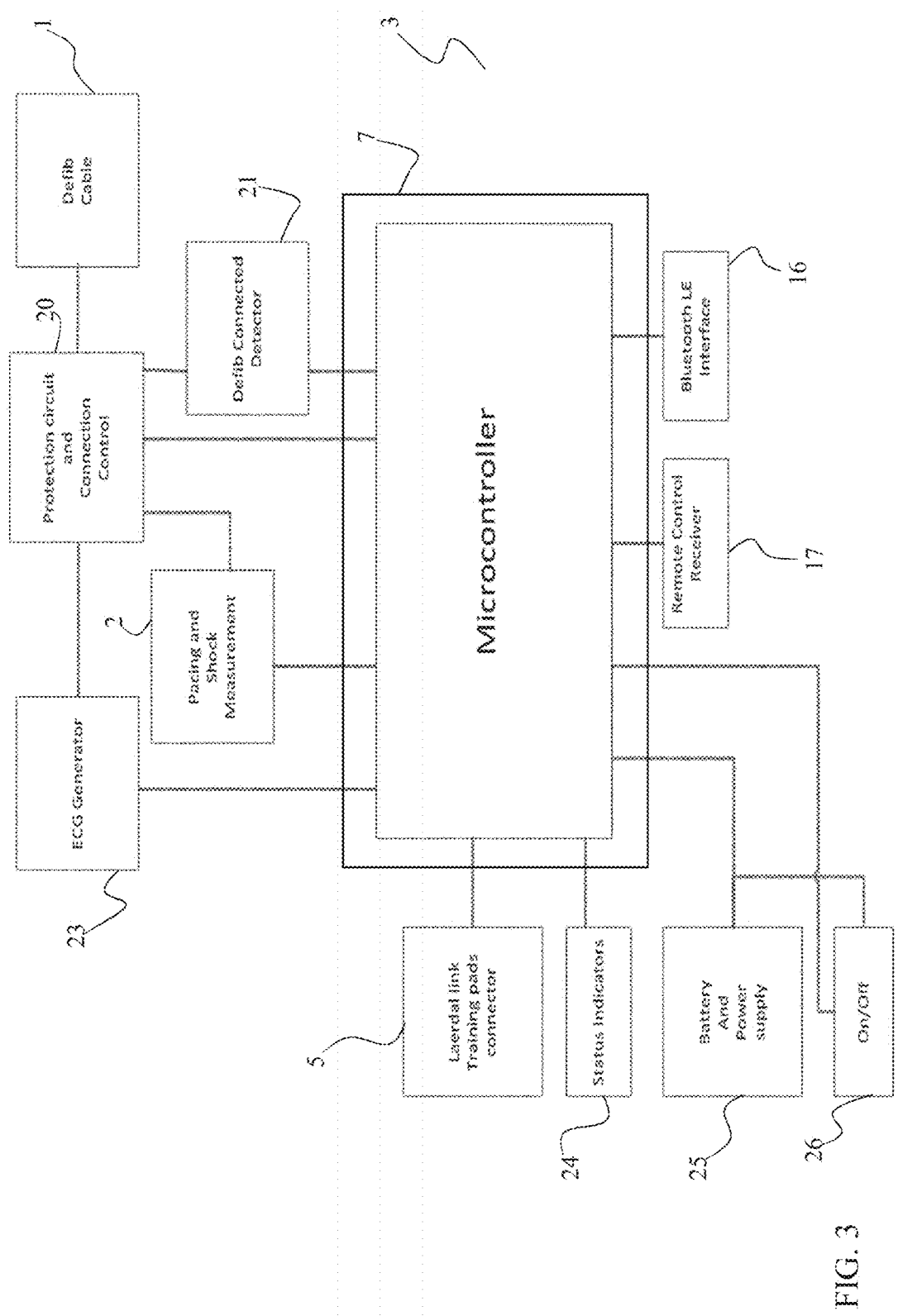
Figure 4:
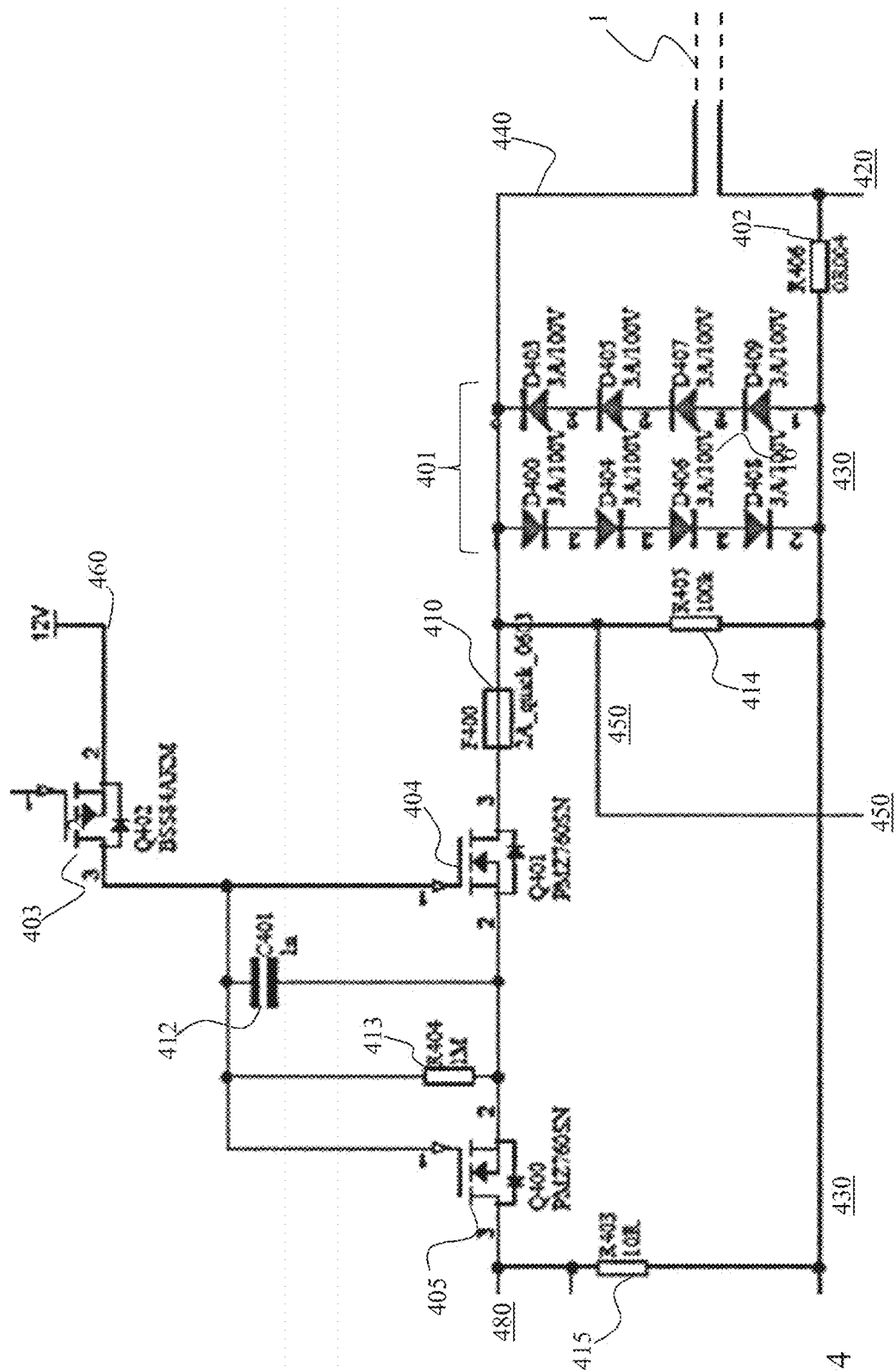
Figure 5:
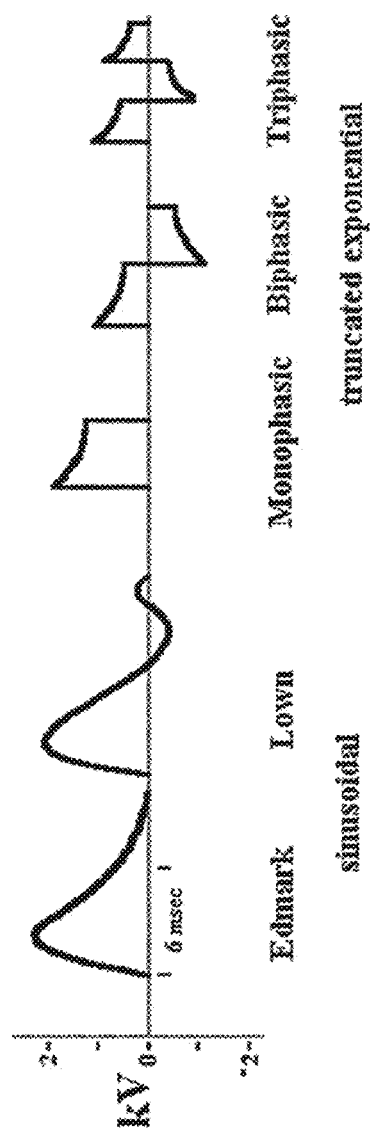
Figure 6:
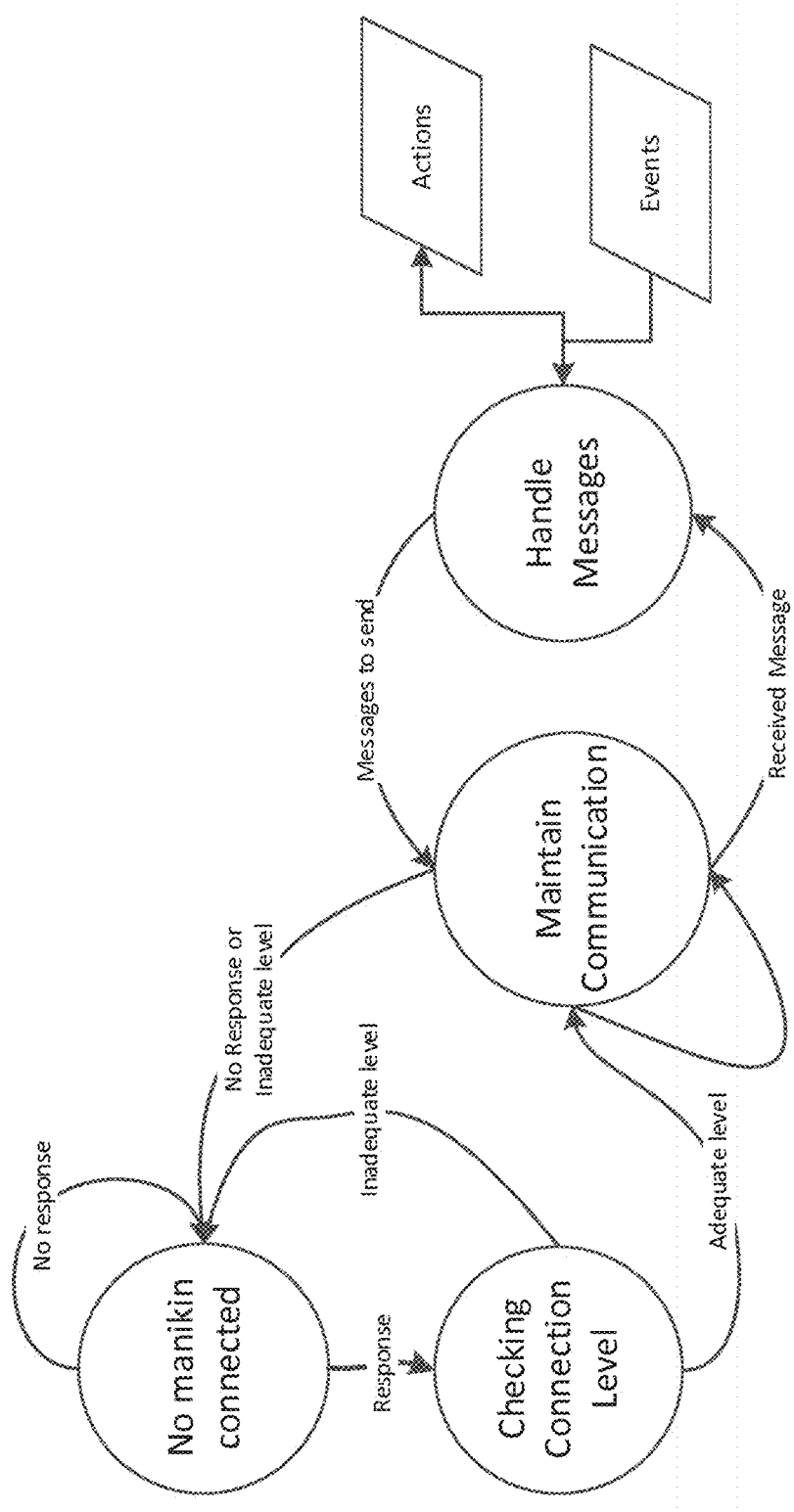

The invention will now be described more detailed, referring to the accompanying drawings as examples, wherein:

FIG. 1 shows a system overview of the invention,

FIG. 2 shows schematically the interface configuration of the system according to the invention, FIG. 3 shows a block diagram of various modules included in the invention, FIG. 4 shows a detailed circuit diagram of the defibrillator interface of the adapter of the present invention, FIG. 5 shows examples of waveforms that is supported by the system and adapter of the present invention, and FIG. 6 shows schematically the manikin communication of the system according to the invention.

The examples in the following description are purely for understanding the functioning of the present invention and are therefore non-limiting to the scope of the patent claims. Furthermore, the drawings may not necessarily be to scale—this anyway not affecting the generality, scope or any of the features of the invention.

FIG. 1 shows the system of the invention in overview. It comprises a signal and resistance cable 1, which is connected to a defibrillator 2. At the other end of the cable 1 is an adapter 3, which is configured to measure a defibrillator shock from the defibrillator 2. The adapter comprises a temperature sensor 13, which is adapted to give a warning if the temperature in the cable 1 gets above a specific value, alternatively the temperature of the cable can be calculated based upon the measured energy absorbed during use.

The adapter 3 also comprises a defibrillator interface 4 that is capable of measuring the defibrillator shock and pacing current of the defibrillator 2. The shock of the defibrillator 2 has been substantially reduced in energy by the resistance cable 1 when it reaches the interface 4. The interface 4 is also capable of transmitting ECG signals to the defibrillator 2 and it also comprises an electrode connection switch. Before this switch is closed, the defibrillator 2 senses a high impedance connection. The switch will be activated if a manikin is sensed by the electrodes. When the switch is closed, the impedance will be typical of a patient and the defibrillator 2 will be capable of shock delivery and pacing.

The adapter further comprises a computational unit 7 that is coupled to a link unit 8 for communication with the electrodes 5. The computational unit may comprise a microcontroller 101 or a plurality of microcontrollers, or a system on chip ("SoC") such as nRF51822, or their likes.

The electrodes 5 are separated from the link unit by a safety capacitor isolation 9, to prevent any defibrillator shock voltage that may find its way through the adapter, from reaching the electrodes 5.

The manikin is conveniently equipped with a simulator unit 10 that is capable of producing a simulated ECG and transmit this signal to the adapter electrodes 5 through manikin electrodes 11 placed under the skin 12 of the manikin 6.

The electrodes 5 are training pads that are capable of transmitting low AC currents between the link unit 8 and the manikin 6

The simulator unit 10 within the manikin 6 may further comprise an ECG library representing various conditions of a patient. The condition may be selected by a supervisor on a user interface on the manikin itself. However, another option is to use a remote control, such as a smart phone 14 or a dedicated remote control 15, which can communicate with the adapter 3 via Bluetooth "(RTM)" 16, infra-red transmitter 17 or other means of communication. The adapter may then either send transfer the information on the selection of ECG condition to the manikin via the electrodes 5 or may overrule the manikin and simulate the ECG signal that is sent to the interface 4. If the manikin 6 is simulating the ECG condition, the condition may either be detected by the link unit and transmitted to the computational unit 7, which in turn sends a similar simulated ECG signal to the interface, or the simulated ECG signal may be sent directly from the link unit 8 to the interface 4.

The adapter may be connected to a non-conducting manikin cable and electrodes for use with manikins without communication capability. Alternatively, the non-conducting cable and electrodes could be safely applied to a human training subject. In this use scenario, the adapter would generate ECG to the attached defibrillator unit under control of either the IR remote control 15, or through wireless communication 14.

The adapter may optionally contain an accelerometer 18. The accelerometer 18 could be used to detect the orientation and movement of the adapter and could also be used as an alternative way to activate (turn on) the adapter if movement is detected.

The adapter has conveniently an automatic on/off switch 19 that is detecting defibrillator impedance measurement signal in the interface 4 and turns the adapter 3 on when this type of signal is detected. If the impedance signal is removed, the on/off switch 19 will turn off the adapter 3 after a specified period of time. If the electrodes 5 are removed from the manikin, the electrode connection switch will be deactivated. In addition to an external power supply, the adapter may also comprise an internal power supply such as battery 110.

A further option is at periodic intervals, if there has been no shock or pacing, and no electrode pad are detected, or no commands from remote control or BLE-unit have been given, the adapter 3 will deactivate the electrode connection switch to check if there is an impedance measurement signal present. If no such signal is present, the adapter 3 will turn itself off.

FIG. 2 shows the coupling between the manikin 6 and the adapter 3. Internal electrodes or pads 11 within the manikin 6 is coupled to external electrodes or pads 5 by capacitive coupling through the skin 12 of the manikin. Thereby there are no visible connectors on the manikin and the student will receive a realistic training of placement of the electrodes 5. If the electrodes 5 are not placed so that they can form a capacitive coupling with the internal electrodes 11, the connection to the manikin is not detected. Then the adapter 3 will not provide the defibrillator 2 with an ECG signal and not defibrillation will be possible. The adapter may be configured to signal, by an audible or visible signal, that the electrodes are not properly placed. The electrodes are as similar to real electrodes as possible, e.g., by the use of adhesive to attach the electrodes to the manikin skin.

The adapter 3 will send a carrier signal to one training pad 5 and then listens if the manikin 6 is sending data back. The data is preferably in the form of an asynchronous serial communication. To ensure that the training pads can be safely touched by the students during training, they are isolated from the rest of the adapter by the capacitor isolation 9. When there is no manikin connection detected, the adapter will check for manikin connection at certain intervals, such as every one second. The check may consist of a 125 ms break signal (carrier signal only) and a request for data message.

After a connection has been established, the connection level will be checked before the connection is accepted. This may be done by requesting a 50 ms carrier signal from the manikin and checking the connection level.

A possible procedure for the detection and checking of a manikin connection is shown in FIG. 6.

FIG. 3 shows the adapter 3 in a different schematic representation than in FIG. 1. The computational unit 7 is coupled to the resistance or defibrillation cable 1 via a protection circuit and connection control 20, which forms a part of the interface 4. The protection circuit and connection control 20 is shown in FIG. 4 and will be explained further below. As will be clear to the person skilled in the art that at least some of the blocks shown in FIG. 3, or as discussed in rest of this disclosure, coupled to the computational unit 7 may actually be contained within the computational unit 7 itself. There are usually several types of microcontroller and SoC devices available in the market with functionality varying from one device to another. A person skilled in the art will typically choose an appropriate device such that the device fulfils a desired set of specifications whilst keeping the costs at a minimum. A person skilled in the art will further appreciate that the selection process for an appropriate computational unit is not important for the scope of the invention. Hence, the embodiments shown in this disclosure are discussed without loss of generality and without limiting the scope of the invention.

A defibrillation connection detector 21 is coupled to the computational unit 7 and the protection circuit and connection control 20, for detecting if a defibrillator is connected to the adapter. As explained above a detection of the impedance of a defibrillator will trigger the on/off switch.

Also coupled to the computational unit 7 and the protection circuit and connection control 20 is a unit 22 for pacing and shock measurement and an ECG generator 23. The ECG generator 23 is capable of generating a simulated ECG signal that can be sent to the defibrillator. As the defibrillator 2 is a real defibrillator, the ECG signal has to simulate a possible real human ECG signal. Based on the received ECG signal, the defibrillator will determine the suitable shocking regime for the "patient". The adapter 3 will also simulate a representative impedance for a real human being, so that the defibrillator in all relevant aspects will "see" a real human being.

When a defibrillator 2 is connected to the adapter 3, the defibrillator 2 will initially see a high impedance, indicating there is no patient present.

When the electrode pads 5 are attached properly on the manikin 6, or commands from an infra-red remote control or a Bluetooth "(RTM)" unit says that the electronic pads 5 are on the manikin, the adapter 3 shall present a lower (patient) impedance to the defibrillator 2. The adapter will then also present an ECG signal to the defibrillator 2. The ECG presented to the defibrillator can originate from the adapter or the ECG can be streamed from the manikin by the adapter.

It is assumed that the defibrillator measures impedance, provided by the adapter 3 but perceived as the impedance of a patient, with an AC signal with a frequency between 2 kHz and 100 kHz, and current as low as 10 uA.

The adapter shall also be able to detect the impedance measurement signal from the AED (Automatic External Defibrillator, HeartStart FR2 "(RTM)", which is using a 540 Hz signal.

As stated above the adapter 3 generates an ECG signal to the defibrillator when it is connected. The ECG signal may be generated by the microcontroller 7 as a Pulse Width Modulation (PWM) signal which is low pass filtered and attenuated to ECG level over the a 10Ω connected resistor. During pacing capture, the ECG generator will generate response to pacing.

During pacing, it is important that there is a perceived immediate reaction to the pacing pulse, and that the paced ECG is shown also on the other ECG sources.

This puts a requirement on the response time through the system from detection of a pacing pulse until a pacing QRS (Q wave, R wave and S wave) is generated on all ECG sources. The pacing pulse event including level will be reported over the link unit 8 connection.

As explained above, the ECG signal can be provided from the adapter 3 or the manikin 6. As a third option the ECG signal can be streamed from a wireless device, such as a smart phone via Bluetooth "(RTM)".

Shock energy is measured by sampling the voltage over the low value series resistor.

Since the electrodes 5 are isolated from the defibrillator 2 by the electronics of the adapter 3, the shock from the defibrillator will never reach the electrodes. However, the occurrence of a shock can be communicated to the manikin 6. If the manikin 6 is configured to receive this signal, the manikin 6 may simulate a reaction to the defibrillation shock.

As explained above, training pads 5 are also coupled to the computational unit 7, as well as a remote control receiver 17, such as an infra-red receiver and a Bluetooth "(RTM)" interface 16. There are also status indicators 24, such as LEDs, battery and power supply 25 and an optional on/off switch 26 for forcing shutdown of the adapter 3.

FIG. 4 shows in greater detail the protection circuit and connection control 20. The defibrillator protection circuit has a bidirectional diode bridge 401 that takes the current during a shock. This is a protection circuit that limits the voltage entering the rest of the system in the adapter 3. In addition, there is a fuse 410 protecting the internal circuitry in case the diode bridge should open up or not work as intended. The conductors of the defibrillation cable 1 are connected to net 440 and net 420 respectively. A current sensing resistor 402, typically of a low value, in this example 0.004 ohms, is placed in series between one of the conductors 420 of the defibrillation cable 1 and net 430. Said current sensing resistor is used for measuring the shock energy and current flowing through the defibrillation cable 1 typically by sampling the voltage drop across said resistor, or by measuring the voltage difference between net 420 and net 430. The MOSFETs 403, 404 and 405 shown in this embodiment of the interface circuit function as switches, and are used to create a conductive path between net 440 and net 480. MOSFET 403 controls the gate voltage of MOSFETs 404 and 405, and when 404 and 405 are switched ON, a low impedance path is created between net 440 and net 480.

FIG. 5 shows a selection supported waveforms of the defibrillation shock. Shocking energy is measured as voltage over a small value resistor in series with the defibrillation circuit, where this voltage represent the current in the whole defibrillation circuit.

The energy is calculated as the integration of $I^2*R$ (Current$^2$*Resistance) over the time the shock is delivered.

Different defibrillators have different defibrillation waveforms with variations in voltage and time. The adapter 3 is configured to prioritize accuracy on newer defibrillators with truncated exponential biphasic waveform, sacrificing accuracy on defibrillators with Edmark/Lown waveforms with high voltages.

The accuracy of a derived shock from a defibrillator may vary significantly, often more than 15%. The adapter is configured to account for this variation.

Pacing pulses from a defibrillator is current pulses of a short duration, intended to provoke a heartbeat. On the defibrillator, one can typically set rate and current. Pulse shape and duration may vary from defibrillator to defibrillator. Often the pulses have a truncated exponential shape, where the peak value is set at the pacing current value.

Pacing current is measured as the voltage drop over the connection resistor 415.

It is possible to set a pacing threshold of the adapter 3, which affects its response to pacing pulses. The pacing threshold can optionally be set from the remote control via Bluetooth "(RTM)" or infrared.

The interface or resistance cable to the defibrillator serves as the defibrillation energy deposit. It needs to have a distributed impedance throughout the cable, and have appropriate strength and isolation to serve as a defibrillator cable. A suitable cable can have the following characteristics:
Cable length:Wire: 100 cm+/−3 cm
Total Cable length: 102.5 cm+/−3 cm
Cable resistance: 2×60Ω+/−13%

Since the resistance load is in the cable 1, the adapter 3 can be made very small and light and will appear as an integrated part of the defibrillator cable.

The invention claimed is:

1. A defibrillation training system comprising:
   a module;
   a resistance cable interconnected between a live defibrillation unit and the module; and
   wherein the resistance cable is electrically isolated by the module from a training manikin or a human being coupled to the module and has an impedance that simulates patient impedance and absorbs electric shock pulses made by the live defibrillator unit.

2. The defibrillation training system according to claim 1, comprising a set of training pads adapted to be coupled between the module and the training manikin, the training manikin having an electronic circuit capable of communicating with the training pads, the module having a galvanic isolation that isolates the training pads from the resistance cable, the module comprising an electronic circuit capable of sensing when the training pads are in communication with the electronic circuit within the training manikin.

3. The defibrillation training system according to claim 2,
   wherein the module comprises a measurement circuit that measures the defibrillation shock and a feedback circuit that provides ECG feedback to the defibrillation unit, both prior to and in response to the measured shock.

4. The defibrillation training system according to claim 1, comprising a communication unit that, when a shock has been delivered to the module, communicates the fact that a shock has been delivered to the training manikin, and thus enables the training manikin to respond clinically adequately to the shock condition, and that the training manikin has a storage to store a complete record of a training session.

5. The defibrillation training system according to claim 1,
   wherein the module comprises an ECG generating circuit coupled to the defibrillating unit, the ECG generating circuit being coupled to a feedback circuit, and that the ECG generating unit generates ECG originating from the module, the training manikin, or a wireless unit.

6. The defibrillation training system claim 1,
   wherein the module comprises a wireless communication circuit for communicating with a remote control device.

7. The defibrillation training system according to claim 6, wherein the remote control device is adapted to receive information about the defibrillation shock and is capable of providing patient reaction ECG data to a feedback circuit based on a selected medical scenario of a plurality of medical scenarios stored in the remote control device.

8. The defibrillation training system according to claim 1, wherein the defibrillating unit is connected to the module by a quick connector that allows disconnection of the defibrillating unit from the module.

9. The defibrillation training system according to claim 2, wherein the training pads are configured to form a capacitive or inductive coupling with electrodes inside the training manikin.

10. The defibrillation training system according to claim 9, wherein the electrodes inside the training manikin are arranged under the skin of the manikin.

11. The defibrillation training system according to claim 1, comprising a non-conductive cable connected between the module and the training manikin, thereby providing training options for passive/non-electronic manikins and training on human subjects.

12. The defibrillation training system according to claim 1,
  wherein the module comprises a power-up circuit that detects the presence of a defibrillator impedance measurement signal and when the signal is present powers up the module.

13. The defibrillation training system according to claim 1,
  wherein the module comprises an accelerometer capable of detecting its orientation and movement, and that a change in orientation or detection of movement beyond a pre-set level is used to trigger power-up of the module.

* * * * *